US00PP36916P2

(12) United States Plant Patent
Trees

(10) Patent No.: US PP36,916 P2
(45) Date of Patent: Sep. 2, 2025

(54) ***BUDDLEIA* PLANT NAMED 'Bud18blu20'**

(50) Latin Name: *Buddleia davidii*
Varietal Denomination: Bud18blu20

(71) Applicant: The Conard Pyle Company, West Grove, PA (US)

(72) Inventor: Scott C. Trees, Arroyo Grande, CA (US)

(73) Assignee: THE CONARD PYLE COMPANY, West Grove, PA (US)

( * ) Notice: Subject to any disclaimer, the term of this patent is extended or adjusted under 35 U.S.C. 154(b) by 0 days.

(21) Appl. No.: 18/907,905

(22) Filed: Oct. 7, 2024

(51) Int. Cl.
*A01H 5/02* (2018.01)
*A01H 6/00* (2018.01)

(52) U.S. Cl.
USPC ..... Plt./242
CPC ..... *A01H 6/00* (2018.05)

(58) Field of Classification Search
USPC ..... Plt./242
CPC ..... A01H 5/02
See application file for complete search history.

(56) References Cited

U.S. PATENT DOCUMENTS

PP24,016 P3 11/2013 Werner et al.
PP28,794 P2 12/2017 Wood

*Primary Examiner* — Kent L Bell
(74) *Attorney, Agent, or Firm* — Panitch Schwarze Belisario & Nadel LLP; Stephany G. Small; Travis W. Bliss

(57) ABSTRACT

A new and distinct variety of *Buddleia* plant, referred to by its cultivar name, 'Bud18blu20', is disclosed. The new variety displays blue-colored flowers and dark green-colored foliage. Moderately vigorous vegetation is formed. The growth habit is compact and well-branched. The new variety has low fertility and is well suited for providing ornamentation in the landscape.

2 Drawing Sheets

Figure 1:
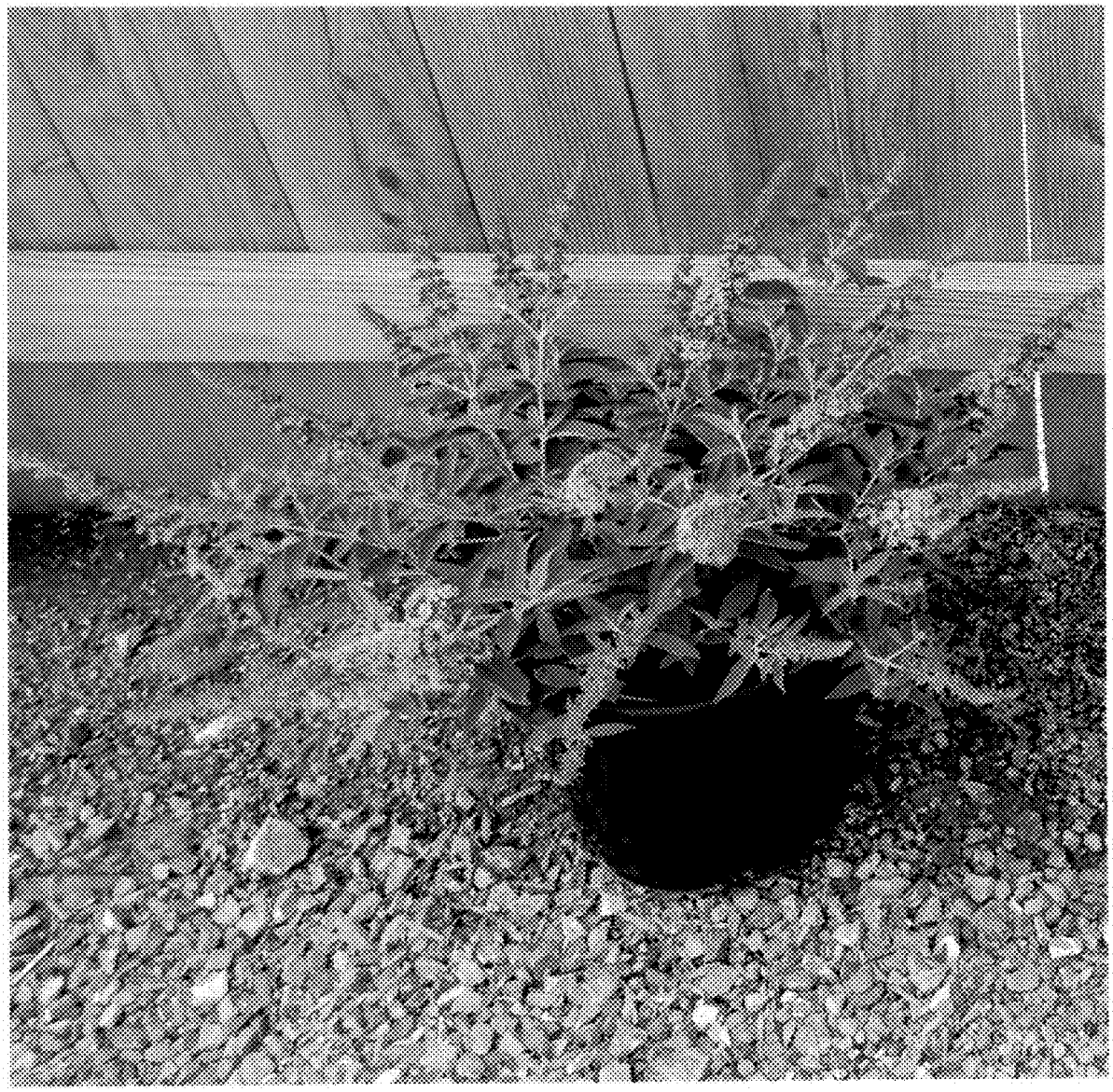

Latin name of genus and species of plant claimed: *Buddleia davidii*.

Variety denomination: 'Bud18blu20'.

STATEMENT REGARDING PRIOR DISCLOSURES BY THE INVENTOR

The first offer for sale of the new variety was Oct. 9, 2023, in the European Union. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of *Buddleia davidii* plant originated in a controlled breeding program in Guadalupe, California during 2016. The new cultivar was created by self-pollination of 'Lilac Chip' (U.S. Plant Pat. No. 24,016).

The parentage of the new variety can be summarized as follows:

'Lilac Chip' x 'Lilac Chip'

The seeds resulting from the above self-pollination were sown and small plants were obtained which were physically and biologically different from each other. The new cultivar was selected as a single flowering plant during May 2017, in a controlled environment in Guadalupe, California.

The new variety has been found to undergo asexual propagation by terminal stem cuttings. Asexual propagation by terminal stem cuttings in Guadalupe, California has shown that the characteristics of the new variety are stable and are strictly transmissible by such asexual propagation from one generation to another. Accordingly, the new variety undergoes asexual propagation in a true-to-type manner.

SUMMARY OF THE INVENTION

It was found that the new variety of *Buddleia* plant of the present invention:

(a) forms blue-colored flowers,
(b) displays dark green-colored foliage,
(c) exhibits a moderately vigorous, compact, and well-branched growth habit, and
(d) has low fertility.

The new variety well meets the needs of the horticultural industry. It can be grown to advantage as ornamentation in parks, gardens, public areas, and in residential settings. Accordingly, the plant is particularly well suited for growing in the landscape. The new variety of the present invention can readily be distinguished from its ancestors. More specifically, the 'Lilac Chip' variety (i.e., the seed and pollen parent) forms lilac-colored flowers, displays gray-green colored foliage and exhibits a very dwarf, spreading growth habit, whereas the new variety forms blue-colored flowers displays dark green-colored foliage and exhibits a compact and well-branched growth habit.

The new variety can also be distinguished from other similar varieties that are commercially available. For instance, the new variety of the present invention can readily be distinguished from the 'SMNBDBT' variety (U.S. Plant Pat. No. 28,794), as the new cultivar displays larger and more abundant flower panicles that bloom earlier in the season, as compared to plants of the 'SMNBDBT' variety. In addition, the new cultivar hides its spent flowers with new flowers during the season well compared to the 'SMNBDBT' variety. Moreover, the new cultivar provides a more upright and dense plant habit compared to the 'SMNBDBT' variety.

The new variety has been named 'Bud18blu20'.

BRIEF DESCRIPTION OF THE PHOTOGRAPHS

The accompanying photographs show as nearly true as it is reasonably possible to make the same, in a color illustration of this character, typical specimens of the plant and plant parts of the new variety. Colors in the photographs may differ slightly from the color values cited in the detailed description, which accurately describes the colors of the 'Bud18blu20' plant. The photographed plants were approximately three months old and grown in one-gallon containers at Cochranville, Pennsylvania in July 2023.

FIG. 1—illustrates a specimen of the plant, displaying the overall growth and flowering habit-side view.

Figure 2:
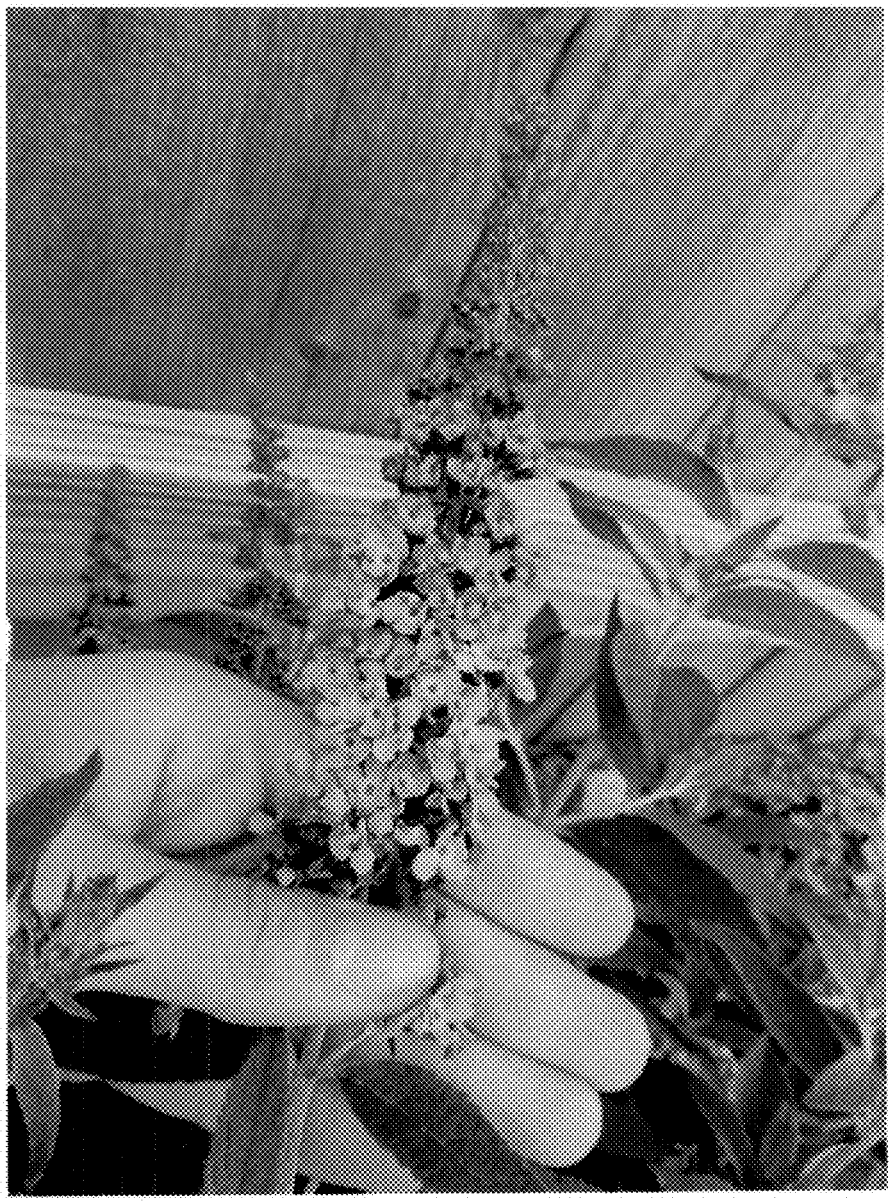

FIG. 2—illustrates a specimen of an inflorescence from a plant of the new variety-close-up view.

DETAILED BOTANICAL DESCRIPTION

The chart used in the identification of the colors is that of The Royal Horticultural Society (R.H.S. Colour Chart), 2015 edition, London, England. The terminology which precedes reference to the chart has been added to indicate the corresponding color in more common terms and The R.H.S. Colour Chart designation used herein represents the closest color observed on the majority of the specified botanical features. The color values were determined in July 2024, under natural light conditions in Cochranville, Pennsylvania. The description is based on the observation of plants produced from cuttings from stock plants and grown in three-gallon containers for approximately 18 months in an outdoor nursery in Cochranville, Pennsylvania. Plants were pinched once after transplant.

Botanical classification: *Buddleia davidii* cultivar 'Bud18blu20'.

Propagation:

*Type cutting*.—Terminal stem.

*Time to initiate roots*.—Approximately 10 to 14 days on average.

*Time to produce a rooted cutting*.—Approximately 24 to 30 days on average.

*Root description*.—Fibrous.

*Rooting habit*.—Freely branching.

Plant:

*Habit*.—Moderately vigorous, compact, and well-branched growth habit.

*Commercial crop time*.—Approximately 2 months from a rooted cutting to finish in a 3-gallon container on average.

*Size*.—Approximately 35.0 cm in height from soil level to top of plant plane on average; and approximately 60.0 cm in width on average.

Branches:

*Branching habit*.—Freely branching, pinching enhances basal branching.

*Quantity of main branches per plant*.—Approximately 9 on average.

*Strength*.—Strong, somewhat flexible, and becomes woody with age.

*Size*.—Length: approximately 24.0 cm on average. — diameter: approximately 4.0 mm on average. — length of central internode: approximately 3.0 cm on average.

*Texture*.—Pruinose and minutely pubescent.

*Color*.—Young stems: Yellow-Green Group N148D. — mature stems: Greyed-Orange Group 174B.

Foliage:

*Number of leaves*.—Approximately 38 per branch on average; and approximately 10 per branched lateral stem on average.

*Fragrance*.—None detected.

*Form*.—Simple.

*Arrangement*.—Opposite.

*Durability to stress*.—Moderate to high.

Leaves:

*Aspect*.—Primarily perpendicular to stem.

*Shape*.—General: lanceolate to oblanceolate. — margin: serrulate. — apex: acute. — base: attenuate.

*Venation*.—Pattern: pinnate, reticulate.

*Size*.—Length of mature leaf: approximately 7.5 cm on average. — width of mature leaf: approximately 2.7 cm on average.

*Texture*.—Upper and lower surfaces: minutely pubescent.

*Color*.—Upper surface of mature foliage: Green Group NN137B. — lower surface of mature foliage: Greyed-Green Group 195A.

*Petiole*.—Shape: rounded, slightly curved. — length: approximately 4.0 mm on average. — width: approximately 1.5 mm on average. — texture: pubescent. — color: Greyed-Green Group 194C.

Inflorescence:

*Quantity*.—Approximately 28 open inflorescences per plant on average; and approximately 500 flowers per inflorescence opening from base to apex.

*Type*.—Terminal panicles, each panicle having about 0 to 2 branches on average; and flowers persistent, facing upward and outward.

*Fragrance*.—Moderate.

*Shape*.—Conical.

*Depth or height*.—Approximately 15.0 cm on average.

*Width*.—Approximately 4.0 cm on average.

*Rachis*.—Strength: strong. — length: approximately 13.0 cm on average. — diameter: approximately 3.0 mm on average. — texture: pubescent. — color: Yellow-Green Group 148D.

Flower:

*Type*.—Single, salverform.

*Bud just before opening*.—Shape: oblong. — length: approximately 6.0 mm on average. — diameter: approximately 1.4 mm on average. — texture: glabrous. — color of petals: Violet-Blue Group 93B.

*Corolla*.—Shape: rotate, commonly 4 petals arranged in a single whorl. — depth: approximately 7.0 mm on average. — width: approximately 6.0 mm on average.

*Petals*.—Shape: rotund. — margin: erose. apex: obtuse. — length from throat: approximately 4.0 mm on average. — width: approximately 3.0 mm on average. — texture of upper and lower surfaces: glabrous. — color of upper and lower surfaces when first and fully open: Violet-Blue Group 94B.

*Corolla tube*.—Length: approximately 3.0 mm on average. — width: approximately 1.0 mm on average. — diameter of throat opening: approximately 1.0 mm on average. — inner surface: texture is lightly pubescent and color is Greyed-Orange Group 169C. — outer surface: texture is glabrous and color is Violet Group 83D.

*Calyx*.—Shape: tubular. — length: approximately 4.5 mm on average. — diameter: approximately 1.2 mm on average.

*Sepals*.—Quantity per flower. commonly 4 on average, fused at base. — length: approximately 1.0 mm on average. — width: commonly less than 1.0 mm. — apex: acute. — margin of free portion: entire. — inner surface: texture: glabrous. color: Green Group 138B. — outer surface: texture: moderately pubescent. color: Green Group 138B.

*Pedicels*.—Strength: strong, flexible. — length: approximately 1.0 mm on average. — diameter: approximately 1.0 mm on average. — texture: densely pubescent. — color: Green Group 143C.

*Reproductive organs*.—Androecium: stamen: absent. anther. absent. pollen: absent. — gynoecium: pistil: commonly 1 per flower; length is approximately 4.0 mm on average. stigma: shape is emarginate; length is approximately 0.5 mm on average; color is Yellow-Green Group 144A. style: length is approximately 1.0 mm on average; color is Yellow-Green Group 145B. ovary: length is approximately 1.3 mm on average; color is Yellow-Green Group 146B. — seed and fruit: none have been observed to date.

Development:

*Blooming*.—Freely flowering under outdoor growing conditions with substantially continuous blooming from late spring through summer.

*Lastingness of individual flower*.—Approximately 7 days on average.

*Tolerance to disease and pest*.—Not observed to date.

The new 'Bud18blu20' plant has not been observed under all possible environmental conditions to date. Accordingly, it is possible that the phenotypic expression may vary somewhat with changes in light intensity and duration, cultural practices, and other environmental conditions, without, however, any variance in genotype.

I claim:

1. A new and distinct variety of *Buddleia* plant named 'Bud18blu20' characterized by the following combination of characteristics:

(a) forms blue-colored flowers, (b) displays dark green-colored foliage, (c) exhibits a moderately vigorous, compact, and well-branched growth habit, and (d) has low fertility, substantially as herein shown and described.

* * * * *